United States Patent
Kluge et al.

(10) Patent No.: US 9,046,449 B2
(45) Date of Patent: Jun. 2, 2015

(54) MEASUREMENT DEVICE FOR THE MEASUREMENT OF FORCES IN STRUCTURAL COMPONENTS

(71) Applicant: Airbus Operations GmbH, Hamburg (DE)

(72) Inventors: Martin Kluge, Königsbrunn (DE); Fabian Sedlmeier, Mainburg (DE); Thomas Becker, Ottobrunn (DE)

(73) Assignee: Airbus Operations GmbH, Hamburg (DE)

( * ) Notice: Subject to any disclaimer, the term of this patent is extended or adjusted under 35 U.S.C. 154(b) by 0 days.

(21) Appl. No.: 13/724,512

(22) Filed: Dec. 21, 2012

(65) Prior Publication Data
US 2014/0007702 A1     Jan. 9, 2014

Related U.S. Application Data

(63) Continuation of application No. PCT/EP2011/003201, filed on Jun. 29, 2011.

(60) Provisional application No. 61/359,411, filed on Jun. 29, 2010.

(30) Foreign Application Priority Data

Jun. 29, 2010   (DE) .......................... 10 2010 025 474

(51) Int. Cl.
*G01L 1/00*     (2006.01)
*G01B 7/16*     (2006.01)
(Continued)

(52) U.S. Cl.
CPC *G01N 3/02* (2013.01); *G01L 19/14* (2013.01); *G01M 5/0041* (2013.01)

(58) Field of Classification Search
USPC ............ 73/862.541, 583, 588, 768, 769, 772, 73/775, 776, 777
See application file for complete search history.

(56) References Cited

U.S. PATENT DOCUMENTS

| 5,182,946 A | 2/1993 | Boughner |
| 6,119,524 A * | 9/2000 | Kobold ........................... 73/727 |

(Continued)

FOREIGN PATENT DOCUMENTS

WO   WO 2012/000662   1/2012

OTHER PUBLICATIONS

International Search Report for Application No. PCT/EP2011/003201 dated Oct. 10, 2011.

*Primary Examiner* — Lisa Caputo
*Assistant Examiner* — Jamel Williams
(74) *Attorney, Agent, or Firm* — Jenkins, Wilson, Taylor & Hunt, P.A.

(57) ABSTRACT

A measurement device for measurement of forces in structural components, having a measurement sensor, which is embodied such that it is connected with the structural component in a force-fit and/or form-fit manner, and generates measurement signals as a function of force transfers in the structural component, the measurement device having a measurement casing upon the measurement sensor. Processing of received measurement signals can occur, and the measurement casing has connecting means, for placing in position and releasable attachment of the measurement casing on the structural component, and the contacting means of the measurement casing can establish contact with the measurement sensor for the reception of the measurement signals.

19 Claims, 14 Drawing Sheets

(51) Int. Cl.
    *G01N 3/02*     (2006.01)
    *G01L 19/14*     (2006.01)
    *G01M 5/00*     (2006.01)

(56) References Cited

U.S. PATENT DOCUMENTS

| | | | |
|---|---|---|---|
| 6,192,759 B1* | 2/2001 | Schoess | 73/583 |
| 6,354,152 B1* | 3/2002 | Herlik | 73/597 |
| 6,581,471 B1* | 6/2003 | Grudzien | 73/753 |
| 7,150,639 B2* | 12/2006 | Fehrenbach et al. | 439/151 |
| 7,174,255 B2* | 2/2007 | Giurgiutiu et al. | 702/35 |
| 7,472,599 B2* | 1/2009 | Vik et al. | 73/627 |
| 7,513,752 B2* | 4/2009 | Boone et al. | 417/44.1 |
| 7,725,269 B2* | 5/2010 | Kessler et al. | 702/35 |
| 8,635,916 B1* | 1/2014 | Loverich et al. | 73/768 |
| 2010/0039104 A1* | 2/2010 | Petersen et al. | 324/207.25 |
| 2010/0100355 A1* | 4/2010 | Marx et al. | 702/183 |
| 2010/0215493 A1* | 8/2010 | Abdallah et al. | 416/23 |
| 2013/0181089 A1* | 7/2013 | Recksiek et al. | 244/99.3 |
| 2013/0327887 A1* | 12/2013 | Dyckrup et al. | 244/99.9 |

\* cited by examiner

MEASUREMENT DEVICE FOR THE MEASUREMENT OF FORCES IN STRUCTURAL COMPONENTS

CROSS-REFERENCE TO RELATED APPLICATIONS

This application is a continuation of and claims priority to PCT/EP2011/003201 filed Jun. 29, 2011, which claims the benefit of the filing date of German Patent Application No. DE 10 2010 025 474.6 filed Jun. 29, 2010 and of U.S. Provisional Patent Application No. 61/359,411 filed Jun. 29, 2010, the disclosures of which applications are hereby incorporated herein by reference.

TECHNICAL FIELD

The invention concerns a measurement device for the measurement of forces in structural components.

BACKGROUND

Measurement devices of this type are, for example, of known art in the measurement of forces in structural components of high-lift systems of an aeroplane. There they are deployed, for example, to ensure that in the transfer of forces onto regulating flaps the maximum permissible forces are not exceeded. The sensors of known art are usually arranged directly in or on the articulations of the force-transferring structural parts, which articulations connect the latter in an articulated manner with other components.

SUMMARY

The above object is achieved by means of a measurement device with the features of the independent claim. Further advantageous embodiments ensue from the dependent claims. Here a measurement device in accordance with the invention for the measurement of forces in structural components has a measurement sensor, which is embodied such that it can be connected in a force-fit and/or form-fit manner with the structural component and generates measurement signals as a function of force transfers in the structural component. Furthermore a measurement casing is provided, placed upon the measurement sensor; this has contacting means for the establishment of contact between the measurement sensor and the structural component so as to receive the measurement signals generated by the measurement sensor, and further processing means for the further processing of the measurement signals received. The measurement casing has connecting means, which are embodied so as to serve the purposes of positioning and releasable attachment of the measurement casing on the structural component. By means of this releasable attachment using the connecting means the contacting means of the measurement casing establish contact with the measurement sensor for the reception of the measurement signals.

An advantage of the invention is that it provides a measurement device with an uncomplicated arrangement which is also easily accessible when being mounted. Moreover, with the measurement devices according to the invention need not be supplied with power, and in addition the measurement signals generated need not be transmitted to further processing elements such as, for example, a control unit. For this purpose terminals are not required on the measurement devices according to the invention and also cables for connection of the measurement with control units are not necessary. As a result, the measurement devices according to the invention can easily be replaced so that a large amount of time and effort in this regard can be saved. In particular, when using the measurement device according to the invention in aeroplanes, the maintenance efforts can be reduced and high costs in the maintenance of the aeroplane saved. Also the replacement of the measurement devices according to the invention is very time-efficient.

In summary it can be stated that a measurement device in accordance with the invention has two parts that are separate from one another, namely a measurement sensor and a measurement casing. This separation of the measurement sensor for the generation of the measurement signals on the one hand and the measurement casing for the accommodation of all further processing means and also the accommodation of contacting means on the other hand, has a plurality of decisive advantages. Thus on the one hand the measurement sensor can be exactly matched to the site of operating. Such measurement sensors can, for example, be directly arranged on force-transferring structural components such as, for example, push rods or pull rods. For example, a measurement sensor can encompass such a rod completely. Since, by virtue of the fact that the further processing means are not arranged in the measurement sensor, such a measurement sensor can be embodied in a very simple and cost-effective manner, the provision of a number of measurement sensors adjacent to one another along the axial extent of a push rod or pull rod can be contemplated. The complex technology, and thus the more cost-intensive part, is arranged in the measurement casing. By virtue of the separate embodiment of the measurement sensor this measurement casing can also be removed from the measurement sensor in a relatively simple manner and replaced by another, for example, by a new measurement casing with new further processing means. The measurement casing thus forms a so-called "line replaceable unit" (abbreviated to LRU), which can be fitted as a black box by maintenance personnel, that is to say, without external access to the contacting means or the further processing means. Here it is crucial that the measurement casing, in correlation with the releasable attachment using the connecting means, so to speak, establishes contact with the measurement sensor automatically. In other words the releasable attachment using the connecting means establishes contact with the aid of the contacting means for the reception of the measurement signals. Accordingly, the maintenance personnel who place a measurement casing upon the measurement sensor, in contrast to the measurement devices of known art, need no longer spend time and effort in executing the establishment of contact themselves, or in ensuring that the contact also functions, since the establishment of contact takes place automatically. The forwarding of the measurement signals from the measurement casing can, by virtue of the defined proportions of the measurement casing, its embodiment as a black box, and the option of the arrangement of the measurement device in regions that are easier to access, be embodied in a significantly simpler and more cost-effective manner.

Under the embodiment of the measurement sensor such that this can be connected in a force-fit and/or form-fit manner with the structural component, various forms of connection are conceivable. Thus it is, for example, possible for the measurement sensor to be applied directly on to the structural component, for example, by means of a galvanic method, or a vapour deposition method. In such cases the use of an adhesive surface and an intermediate polymer film can be dispensed with completely. The inadequate mechanical connection between structural component and measurement sensor that is associated with such adhesive films and the accompanying lack of reliability in terms of the correlation of the measurement signals generated by the measurement sensor with the actual force conditions in the structural component can in this manner be reduced or even avoided altogether. A further possibility is an integral design of the measurement sensor with the structural component. This occurs, for example, if the measurement sensor is laminated into the structural component, in particular if the latter consists of laminated structures with glass fibres and carbon fibres.

The further processing by means of the further processing means of the measurement casing is primarily designed for the purpose of receiving the measurement signals and processing these for use, for example, in a flight control system, or in the controller of the regulating flaps of a high-lift system. Thus, for example, further processing means can be contemplated, which have analogue-to-digital converters, signal amplifiers, or reception and forwarding interfaces. However, the further processing means are also to be understood to include such means that support the measurement process, such as, for example, batteries or capacitors for the supply of energy. Thus, the further processing means can include a multiplicity of individual components.

In a measurement device in accordance with the invention it can be advantageous if the contacting means are designed for the wireless transfer of the measurement signals from the measurement sensor to the measurement casing. Such wireless transfers have, in particular, the advantage that mechanical defects of the contacting means as a result of the absence of mechanical components are excluded. Wireless transfer can, for example, take place capacitatively, or also inductively. In the case of capacitative transfer the measurement sensor forms one part of the capacitor while the second part of the capacitor is provided in the contacting means. Depending upon the force conditions in the structural component and the measurement signals thus generated in the measurement sensor the measurement signal is transferred via the capacitative coupling through the contacting means to the further processing means in the measurement casing. In the case of inductive transfer the phenomenon of inductance is utilised in a similar manner for the transfer of the measurement signals by means of the contacting means onto the further processing means of the measurement casing. Here the connection is made in an advantageous manner in the near field, e.g. ISM bands in the region of 13.56 MHz, or frequencies of less 135 kHz. Contact can also be established by means of an ACA (anisotropic conductive adhesive). Here, for example, with the application of pressure by the connecting means an anisotropic conductivity would be achieved. In this manner the corrosion of the contact surfaces would be avoided.

Alternatively or in parallel to wireless transfer it can also be advantageous if in a measurement device in accordance with the invention the contacting means are designed for a tangible form of transfer of the measurement signals from the measurement sensor to the measurement casing. Such a tangible form of transfer can, for example, be embodied in terms of mechanical components such as, for example, the establishment of contact with a spike or with a sprung pin. A spike can, for example, be designed such that in the generation of the releasable connection with the connecting means between the measurement casing and the measurement sensor it is pressed into the measurement sensor. Here the spike can penetrate through protective or insulating layers of the measurement sensor and directly enters into the measurement sensor material as the material that generates the measurement signals. By means of the releasable attachment using the connecting means the spike thus makes contact with the measurement sensor material of the measurement sensor and thereby generates the contact enabling the reception of the measurement signals by the further processing means in the measurement casing. The use of sprung pins or otherwise mounted mechanical elements, which in correlation with the releasable attachment using the connecting means make contact with the measurement sensor, in particular its measurement sensor material, can also be contemplated within the framework of the present invention.

In some operating situations it can be advantageous if the measurement device is embodied such that for this purpose the measurement sensor is designed to be formed integrally with the structural component. In particular in the case of structural components, which consist of glass fibre and/or carbon fibre components, e.g. GFP or CFP structural components, an integral design can be achieved in a relatively simple manner, in which the measurement sensor is at least partially integrated in the production process of the structural component. In the use of connecting means that can flow, such as, for example, casting resins, the measurement sensor can be inserted into a mould for the structural component and during the subsequent casting or laminating process it can be connected in a force-fit and form-fit manner with the structural component. Alongside the simple operations of this form of production further advantages are to be noted. Thus an ideal force-fit and form-fit form of connection between measurement sensor and structural component is provided in this manner, since the measurement sensor has, so to speak, become a part of the structural component. The reliability of such a force-fit and form-fit form of connection, in terms of the reproduction of the actual force conditions in the structural component by the measurement signals generated, is extraordinarily high. In addition, an integral embodiment of this type is of advantage since the measurement sensor is located in the structural component in a protected manner. External effects caused by the weather or wear of the structural component only reach the measurement sensor after a time delay, or not at all, as a result of which the latter remains essentially constant in its functionality, even after extended operating. In an embodiment of this type it can be particularly advantageous if, for purposes of transfer of the measurement signals to the further processing means of the measurement casing a non-tangible establishment of contact, for example, wireless transfer, is made by means of the contacting means in the measurement casing. In this manner there is no need to damage the outermost layer of the structural component.

Alternatively, or also in combination with an integral design of the measurement sensor individual regions or layers of the measurement sensor, or even the whole measurement sensor, can also be designed such that they are deposited on the structural component. Such deposition processes can be generated, for example, by the vapour deposition of materials and the precise layers that thereby form on the surface of the structural component. The vapour deposition can also be accompanied by chemical reactions, so that in addition to the form-fit form of connection as a result of the vapour deposition, a force-fit form of connection also occurs, for example, as a result of chemical bonding in addition to the adhesion forces. After or during the vapour deposition process, or between distinct vapour deposition processes for distinct layers of the measurement sensor, a micro-structuring process can take place, which generates advantageous structures in the measurement sensor, in particular in the measurement sensor material. In the case of multi-layer measurement sensors, which have a layer of measurement sensor material, for example, a piezo-electric material, multi-layer structures can in this manner be achieved, in which the measurement sensor material layer has a structure that is matched to the force conditions anticipated in the structural component, such that it generates measurement signals in an ideal manner that correlate as far as is possible with the real force conditions in the structural component. For example, microstructures in the form of comb structures or thread-like regions that run along the anticipated main force direction can be contemplated.

A measurement device in accordance with the invention can have a measurement sensor that is embodied over a large surface area, so as to cover a larger surface area of the structural component than the measurement casing itself. In particular, when using vapour deposition processes or during integral embodiment of the measurement sensor with the structural component a large surface area configuration for the measurement sensor can be ensured relatively simply. During the vapour deposition process a larger surface area of the structural component is simply subject to vapour deposition, and the layers necessary for the generation of the measurement sensor are therefore applied over a larger surface area. Also lamination into the structural component can take place over a large surface area in a similar manner. Here the additional costs for the large surface area of the measurement sensor are relatively low in comparison to the more expensive electronics that are arranged in the measurement casing. In this manner more complex structures of structural components, such as, for example. essentially cylindrical pull rods or push rods can also be equipped with measurement sensors over a large surface area, while the measurement casing can be arranged at the most suitable position for this purpose in terms of geometry. Here under the term "large surface area" it is also to be understood that a multiplicity of measurement sensors can be provided directly adjacent to one another, or spaced apart from one another, so as to obtain thereby a large surface area with measurement sensors on the structural component. This has furthermore the advantage that during the course of the life of the structural component, for example, at defined maintenance intervals, the measurement casing can be removed from one measurement sensor and placed upon another. Thus wear during the measurement, in particular in the region of the contacting means is compensated for such that with the use of a single measurement casing a multiplicity of measurement sensors can be used over the service life of the structural component. Also, such a structural component can be used in a modular manner, since the measurement casing can be mounted at different sites depending upon the actual operating location and in accordance with actual operating conditions. The ideal geometric site for the measurement casing, which changes depending upon the operating conditions, can thus be ensured with a single component for all operating conditions.

It can be advantageous if the measurement sensor of a measurement device in accordance with the invention is equipped with at least one piezo-electric element for purposes of generation of the measurement signal. The use of piezo-electric elements as piezo-electric material for the design of the measurement sensor has the advantage that in a very simple manner, and in particular, independently of external energy sources, measurement signals can be generated in the form of parameter modifications that can be measured electrically. A further advantage is the cost-effective operability of piezo-electric elements, which, moreover, can also be connected with the structural component in a simple force-fit and/or form-fit manner. Thus the piezo-electric elements are advantageously made of a material that enables a vapour deposition process to be used for the measurement sensor material layer. Here the whole layer of the measurement sensor material can be produced from a piezo-electric material, and can advantageously surround the structural component in the whole region of the measurement sensor.

Similarly, it can be advantageous if the further processing means has a wireless device for transmitting the signals received from the measurement sensor. The further processing means together with a wireless device have the advantage that a measurement casing of this type need no longer be provided with any cables for the transmission of the measurement signals and/or the further processed signals to the necessary location, for example, a control unit or a central processing unit. As methods of wireless transfer both so-called "near field communication" (NFC) or other near field wireless systems such as, for example, Bluetooth wireless systems, can be used. However, other wireless systems, for example in the high frequency range, can also be contemplated, although care must be taken that the wireless signals do not have a negative effect on other sensitive control elements, in particular the flight control systems, when used on structural components for aeroplanes. The dispensation with mechanical connections to the measurement device that is possible in this manner increases the versatility of operation of the measurement device in accordance with the invention even further.

So as to improve the further processing means even further it can be advantageous if in the case of a measurement device in accordance with the invention these are equipped with at least one board. This board can host a variety of electronic components, and can thereby condense them together. Thus signal amplifiers for the application of the received measurement signals can be contemplated, as can analogue-to-digital converters (A/D converters), which convert the received analogue measurement signals into digital signals for processing in downstream control units. The provision of a battery as a power supply for the electronic components arranged in the measurement casing can also be contemplated. However, the measurement casing can also fulfil a significant number of further functions on its board, for example, it can provide an evaluation unit, a pre-processing unit for the signals, or even a control unit for the control of downstream structural elements, such as, for example, regulating flaps. Furthermore, the further processing means, in particular the board, can have an interface for the forwarding of the signals. This interface, in addition to the wireless connection already described, can also be a mechanical interface, which, for example, is designed in the form of plug-in connections by means of snap-latch connectors. By the arrangement of a defined interface in the measurement casing the latter can be designed significantly more simply and, in particular, in a standardised manner. This leads on the one hand to easier utilisation of the interface and, on the other hand, to a more secure connection with the signal cables fitted to the interface.

In particular during long-term operation of measurement devices in accordance with the invention it can be advantageous if the measurement casing is sealed with sealing agents against the penetration of solid or fluid components. Such sealing agents can be embodied, for example, in the form of O-rings, flat plastic seals, or metal seals. They bring with them the advantage that even in long-term operation damaging substances in the form of solids or fluids cannot penetrate into the measurement casing to have a negative effect on the electronic components contained therein, in particular, the contacting means and the further processing means. The measurement casing has accommodation regions for these sealing agents, so that the sealing agents can exercise their sealing action in an ideal manner. These accommodation regions can be grooves, depressions or also steps, which in terms of their surfaces are matched to the design of a sealing line.

Similarly, it can be advantageous if the measurement casing of a measurement device in accordance with the invention is embodied in the form of a collar that can encompass the structural component. The provision of an encompassing collar has the advantage that the structural component is completely independent of the collar of the measurement casing. Instead the collar is matched to the shape of the structural component, for example, on a pull rod or push rod. When a collar is provided, the attachment of the measurement casing to the structural component takes place, for example, by an increase of the friction between collar and structural component, that is to say, by compressing the collar, so to speak, onto the structural component. This compression can take place over a large surface area, that is to say, over the whole contact region between structural component and measurement casing, although individual regions, for example with the use of grub screws, can also be contemplated; with an increased level of friction, that is to say, by means of compression, these achieve the releasable attachment of the collar, and thus of the measurement casing, to the structural component. A further advantage of the design in the form of a collar is that no adaptation of the structural component is necessary for the attachment of the collar. In particular no bores or threads are necessary, which would have an adverse effect on the force paths in the structural component. In this manner even a refurbishment of already existing components is possible without these having to be redesigned and, in particular, re-certificated for operational use. In particular when using the measurement device for high-lift systems of aeroplanes this is of great advantage, since the certification of new components is particularly intensive in terms of time and cost.

In particular when using a collar as a measurement casing, but in other variants of a measurement device in accordance with the invention also, it can be of practical benefit for the connecting means of the measurement casing to have a hinge for purposes of opening and closing the collar. Here the use of a hinge has the advantage that it takes the form of a very simple connecting means, which in particular does not contain any releasable or loose parts. Rather it is the case that the maintenance personnel, when positioning the measurement casing on the structural component around the measurement sensor, have a reduced number of parts to manage, since the hinge is permanently connected with the measurement casing, or the individual segments of a measurement casing. Moreover, the functionality of a hinge is intuitively accessible and defines the movement of the individual segments of a measurement casing relative to one another very clearly. Incorrect installations, which can lead to inadequate measurement results or to other defective functioning of the measurement device, are in this manner more or less completely excluded.

In some forms of embodiment it can be advantageous if the measurement device has a measurement casing that is composed of a plurality of segments. The provision of a plurality of segments for the measurement casing has the advantage that even complete structural component geometries can be provided with one measurement casing. In particular when encompassing the structural component, for example by means of a measurement casing in the form of a collar, embodiment in the form of segments can bring advantages with it. In the simplest case, in particular when using a hinge between two segments of a measurement casing, the segments of the measurement casing are opened up by means of the hinge, the measurement casing is positioned around the structural component in the form of a push rod or pull rod, and the segments are closed up once again by means of the hinge. After the segments are closed up, further connecting means, such as for example a screw or grub screws serve to increase the surface pressure between the measurement casing and structural component, so that the measurement casing is attached to the structural component in a more releasable manner.

A measurement device in accordance with the invention can be designed such that the connecting means has at least one threaded means of connection, which is embodied such that individual segments of the measurement casing can be connected with one another such that the measurement casing is attached to the structural component by means of surface pressure. This threaded means of connection can be understood to achieve a connection of the two segments with one another, no that, for example, when designed as a collar the measurement casing has a central opening diameter, which is reduced by the tightening of such a connecting screw. This reduction, so to speak, shrinks the measurement casing onto the structural component by means of the screw. The surface pressure thereby achieved serves to provide the releasable attachment of the measurement casing to the structural component. The reduction of the diameter of the central opening can however also take place in the form of grub screws, which deform regions of the measurement casing plastically or elastically, and thereby generate the desired pressure between measurement casing and structural component.

Furthermore, it can be advantageous if a measurement device in accordance with the invention has individual segments of the measurement casing that are provided with contact surfaces. These contact surfaces serve the purpose of transferring measurement signals or further processing signals between the individual segments of the measurement casing. The segmental embodiment of the measurement casing thus serves the purpose of equipping individual segments with different functionalities, in other words with different electronic components. In addition to the simpler installation of the measurement casing, this has the further advantage that in the event of faults in the electronic component in one segment of the measurement casing only this one segment has to be replaced. Thus, for example, in the event of the failure of the battery in the measurement casing, or if the battery simply becomes exhausted, the appropriate segment can be removed from the rest of the measurement casing and replaced.

Furthermore it can be advantageous if the interior of the measurement casing is externally accessible in a simple manner. This can, for example, be achieved if the measurement casing has a closable cover. Here once again care is to be taken that sealing agents are provided, by means of which any penetration of solids or fluids into the interior of the measurement casing via the cover, or gaps between the cover and the rest of the measurement casing, is avoided. This cover can, for example, be configured such that it can only be opened when the measurement casing is not placed in position. In the placed in position state, that is to say, in the state in which the measurement casing is attached to the structural component around the measurement sensor, the cover can, for example, be located in an inaccessible region. This ensures that on the one hand a simple installation of the electronic components in the measurement casing can take place, but that this installation cannot inadvertently be impaired by untrained maintenance personnel when the measurement casing has been placed in position.

As has already been stated with regard to the individual advantageous embodiments of the present invention, a measurement device in accordance with the invention can be deployed particularly advantageously in the adjustment mechanisms of regulating flaps of a high-lift device of an aeroplane. Such high-lift systems usually possess a main wing surface, which primarily accommodates the air loads impacting onto the high-lift device, and thus generates the major part of the lift. However, under certain flight conditions of aeroplanes particular requirements have to be placed on the high-lift system. Thus in cruise flight, for example, an air resistance that is as low as possible is required so as to minimise the fuel consumption of the aeroplane. For takeoff and landing, however, a lift force that is as large as possible is required. For these cases regulating flaps, which are sometimes also designated as landing flaps, are present on the high-lift device; these can be moved relative to the main wing surface. This movement, in other words the adjustment of the regulating flaps, usually takes place by means of actuators that are controlled by hydraulic systems. These actuators can, for example, have kinematic lever mechanisms, which transfer the main loads of the regulating flap of a high-lift device, wherein however at least one active lever element must be provided, via which the adjustment force is transferred onto the regulating flap. A measurement device in accordance with the invention can now be fitted in an advantageous manner to this active lever element, or also to other elements of the kinematic lever mechanism. Here it can have a communicative connection with the hydraulic controller of the actuator and/or with the flight control system itself. In this manner overload conditions in the actuator can be prevented, or at least their duration can be minimised. This leads to lengthened service lives for the structural component on the one hand and to improved reliability on the other hand. Thus, for example, after a prescribed number of measured maximum loads a change of the monitored structural component can be provided so as to anticipate any possible failure.

BRIEF DESCRIPTION OF THE DRAWINGS

The invention is elucidated in more detail with the aid of the accompanying drawings. Here the terms that are used: "on the left", "on the right", "above" and "below" relate to the drawings when orientated such that reference symbols can be read in a normal manner. In the figures.

DETAILED DESCRIPTION

In an exemplary embodiment of the invention, apparatus and methods described hereinabove are employed to reduce the mechanical and functional efforts with regard to manufacturing, installing and use of a measurement sensor in particular in an airplane. The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively or additionally, portions of the invention described/depicted as a single unit may reside in two or more separate physical entities which act in concert to perform the described/depicted function. Alternatively or additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. Specifically, features described in the context of a method can be used to characterize an apparatus and features described in the context of an apparatus can be used to characterize a method. The scope of the invention is limited only by the following claims. In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb. All publications and/or patents and/or product descriptions cited in this document are fully incorporated herein by reference to the same extent as if each had been individually incorporated herein by reference.

Figure 1:
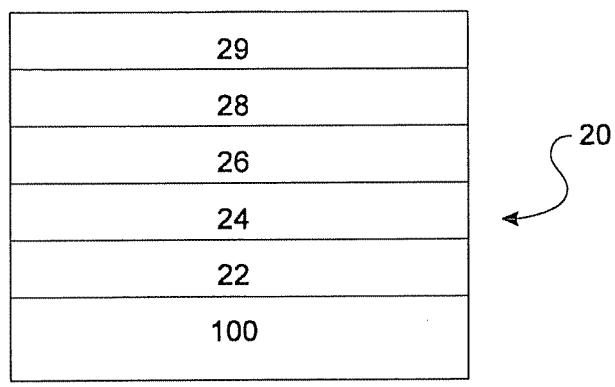
FIG. 1 shows a cross-section through a form of embodiment structured in the form of layers of a measurement sensor in accordance with the invention.

In FIG. 1 the layered structure of a measurement sensor 20 is schematically represented. This measurement sensor 20 is constructed from various layers, wherein starting from the bottom the structural component 100 is to be seen as the first. Placed on top of that is a bonding agent 22, followed by an insulation layer 24. Placed on top of that is a layer of measurement sensor material 26 and also a contact layer 28. At the top the layered structure is completed with a passivation layer 29. The two lower layers, that is to say, the bonding agent 22 and the insulation layer 24, serve to provide a force-fit form of connection of the measurement sensor 20 with the structural component 100. The layer with the measurement sensor material 26 serves to generate the measurement signals and in this case is produced from a piezo-electric material. The contact layer 28 serves the contacting means of the measurement casing 30 and transfers the generated measurement signals of the measurement sensor material 26 to the contacting means 32 of the measurement casing 30, which in this figure is not yet represented. At the top is finally located the passivation layer 29, which completes the measurement sensor 20 and protects it from negative environmental effects. The layers of this structure have been applied in sequence by means of a vapour deposition method onto the structural component 100.

Figure 2:
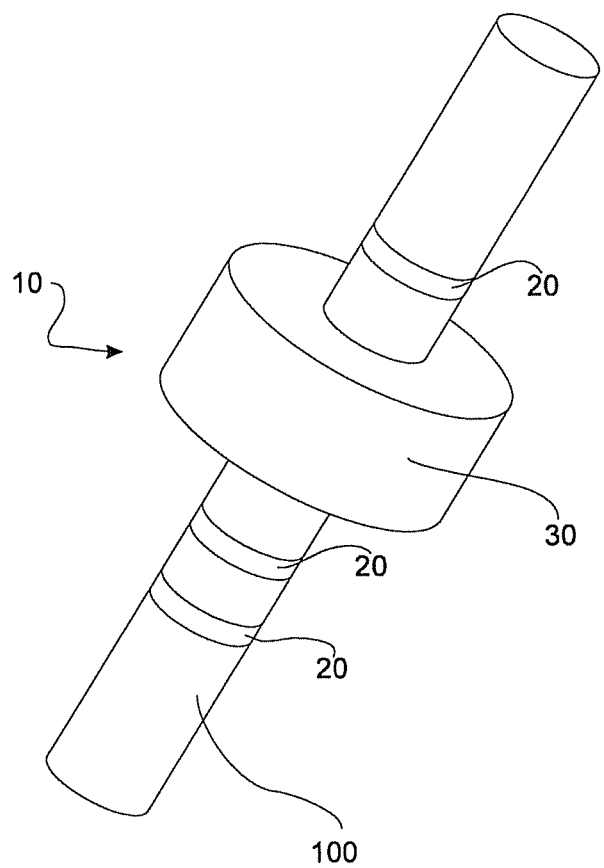
FIG. 2 shows a structural component with a plurality of measurement sensors and a measurement casing placed in position.

FIG. 2 shows an isometric representation of a form of embodiment of the present invention. The structural component 100 is embodied as a pull and push rod, which possesses an essentially cylindrical shape. The pull/push rod as a structural component 100 is in this case provided with four measurement sensors 20, which with a small axial extent of the measurement sensor 20 along the structural component 100 completely surround the latter in the circumferential direction. The measurement sensors 20 are located in the form of bands around the structural component 100. Of the four measurement sensors 20 three measurement sensors 20 can be discerned, since these are not provided with a measurement casing 30, but serve as redundant measurement sensors 20, upon which the measurement casing 30 can be placed later at subsequent maintenance intervals. The measurement casing 30 is placed upon the fourth and therefore invisible measurement sensor 20 and at this location is releasably attached to the structural component 100. In this manner the contacting means 32, which in this figure also cannot be discerned, are brought into contact with the measurement sensor 20, so as to transfer the measurement signals generated. The measurement casing 30 at maintenance intervals or in the event of an acute failure of the contacted measurement sensor 20 can be released, pushed further along onto an adjacent measurement sensor 20, and reattached. A complete removal of the measurement casing 30, which here is designed as a collar, is not necessary for this purpose.

Figure 3:
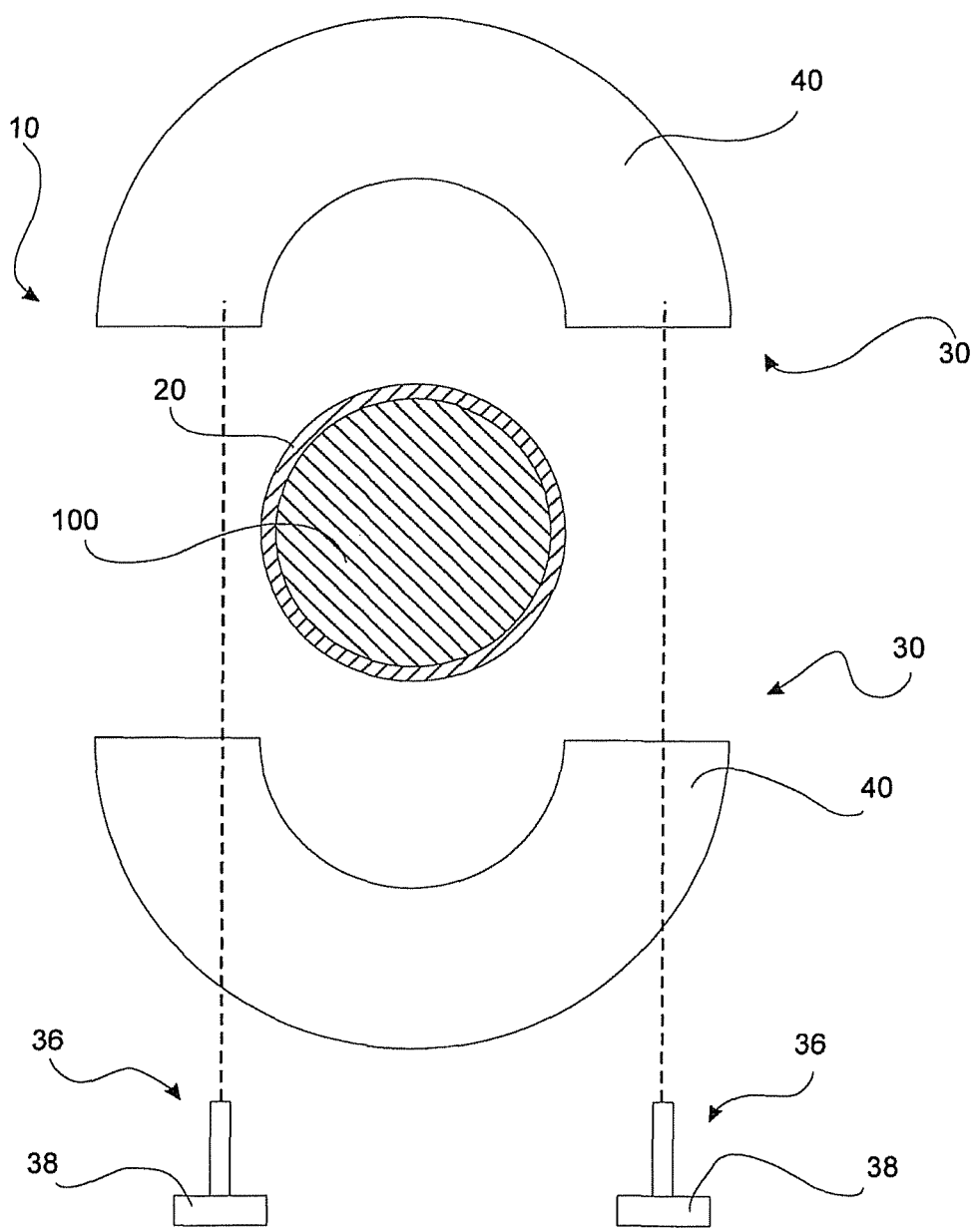
FIG. 3 shows a cross-section through a form of embodiment of a measurement device in accordance with the invention.

In FIG. 3 a possible form of embodiment of a measurement device 10 in accordance with the invention is represented in cross-section. In this example of embodiment the measurement casing 30 is constructed from two segments 40. These two segments 40 when seen together are designed in the form of a collar, which can be positioned around the structural component 100. Likewise, in the cross-section it can be discerned that the structural component 100 in this section is fully surrounded by the measurement sensor 20. So as to attach the measurement casing 30 to the structural component 100 in a releasable manner, the two segments 40 are positioned around the structural component 100 and thus also around the measurement sensor 20. In the next step two connecting means 36 in the form of threaded means of connection 38 such as bolts or screws serve to connect the two segments 40 of the measurement casing 30. The two screws 38 thus screw the two segments 40 together and thereby reduce the internal diameter of the opening of the measurement casing 30, through which the structural component 100 runs. By the reduction of this internal diameter there arises an increase in the level of friction, in particular a surface pressure is generated between the individual segments 40 of the measurement casing 30 on the one hand and the structural component 100 and thereby the measurement sensor 20 on the other hand. By means of this surface pressure, the measurement casing 30 is releasably attached to the structural component 100 and at the same time contacting means 32, which are not yet represented here, make contact with the measurement sensor 20 for the reception of measurement signals.

Figure 4:
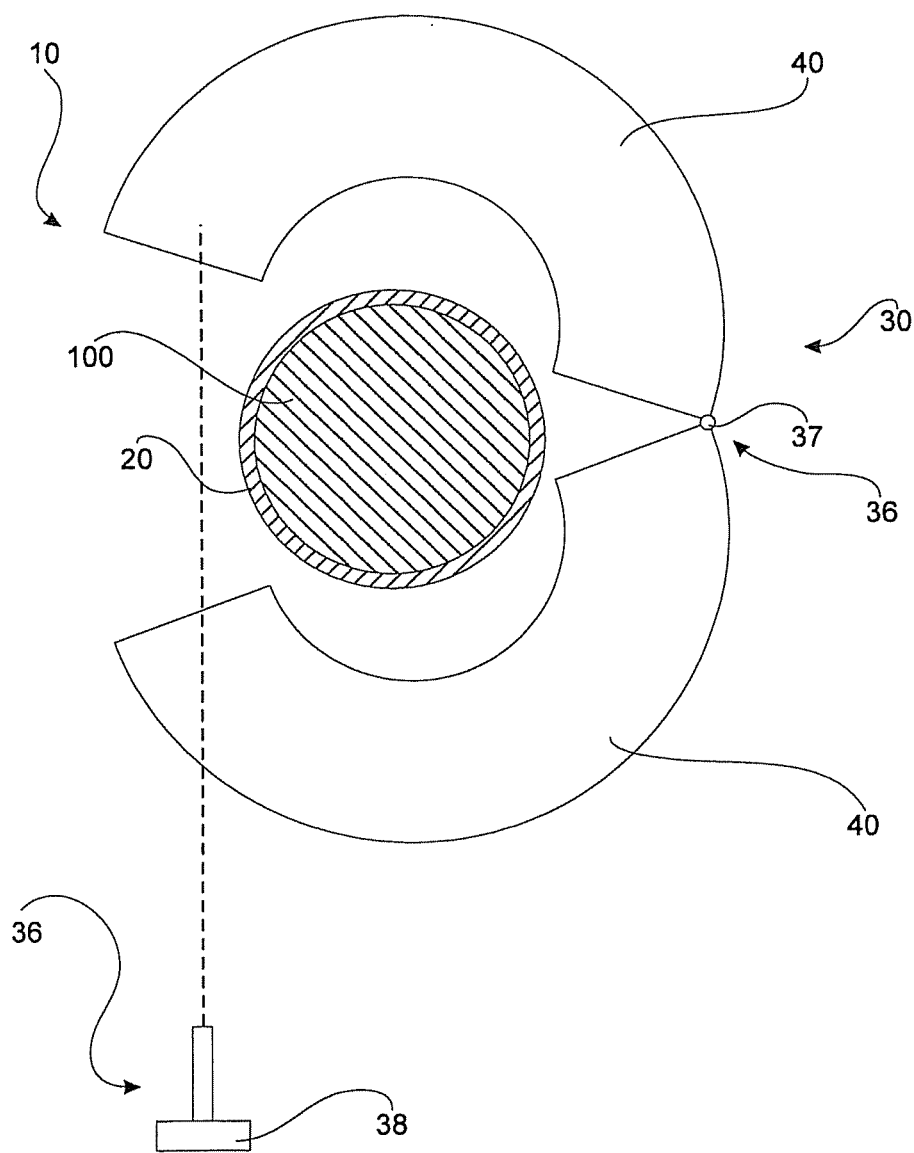
FIG. 4 shows a cross-section through a further form of embodiment of a measurement device in accordance with the invention.

FIG. 4 shows an alternative form of embodiment, wherein the measurement casing 30 is again constructed from two segments 40, and is embodied in the form of a collar. The two segments 40 are connected together by a hinge 37, which is part of the connecting means 36, so that the two segments 40 of the measurement casing can be closed up relative to one another. Here the axis of rotation of the hinge 37 runs alongside the axis of symmetry of the cylindrically designed structural component 100. In this manner the central opening, which is formed in the measurement casing 30 by the two segments 40, can be opened and closed by means of the hinge 37 on the side opposite to the hinge 37.

FIG. 4 shows the opened state of the measurement casing 30. In this state the measurement casing 30 in the form of a collar is positioned around the structural component 100 and the two segments are then moved towards each other via the axis of rotation of the hinge 37, so that the two segments and thus the measurement casing 30 completely enclose the structural component 100 and thus the measurement sensor 20 also. In contrast to the example of embodiment as per FIG. 3 only a single threaded means of connection 38 is necessary in this case. This again serves the purpose of reducing the internal diameter of the internal opening of the measurement casing 30 such that an increase in the level of friction is generated, in particular a surface pressure is generated between the individual segments 40 of the measurement casing 30 and the structural component 100 to the effect that the measurement casing 30 is releasably attached to the structural component 100. In comparison to the embodiment as per FIG. 3 the attachment in this manner is even simpler, since not only are the segments 40 of the measurement casing 30 exactly aligned with one another via the hinge 37, but also only a single threaded means of connection 38 has to be tightened so as to achieve the releasable attachment. In addition to the simpler and faster releasable attachment of the measurement casing 30 to the structural component 100 the correct alignment of the measurement casing 30 with reference to the structural component 100 and thus also to the measurement sensor 20 is thus also ensured.

Figure 5:
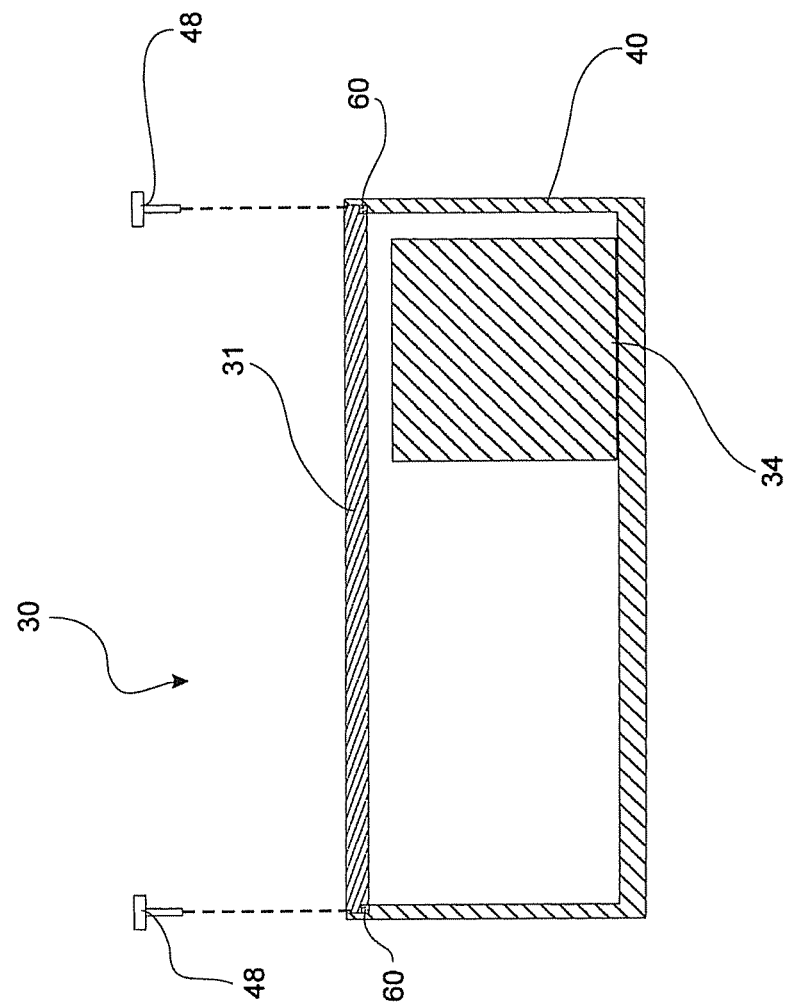
FIG. 5 shows a cross-section through a part of a measurement casing of a form of embodiment of a measurement casing with a cover.

FIG. 5 shows in cross-section a part of a segment 40 of a measurement casing 30. This measurement casing 30 is provided with a cover 31, which can also be closed with two threaded means of connection 48. If the cover is opened the measurement casing 30 can be filled with electronic components of the further processing means 34, and these electronic components in the interior of the measurement casing 30 can be prepared for their deployment, in particular, they can be wired up to one another. The cover 31 is then placed upon the measurement casing 30, and attached with the threaded means of connection 48, which here, however, do not serve as connecting means 36. So as to ensure that the no damage can be inflicted on the interior of the measurement casing 30, in particular on the further processing means 34, the casing is sealed against the penetration of solids and fluids with the aid of sealing agents 60. Here the sealing agents 60 are sealing agents of an elastic material, which are compressed as a result of placing the cover 31 in position, and tightening down the cover 31 by means of the threaded means of connection 48, and thus form a laminar sealing line along the periphery of the cover 31.

Figure 6:
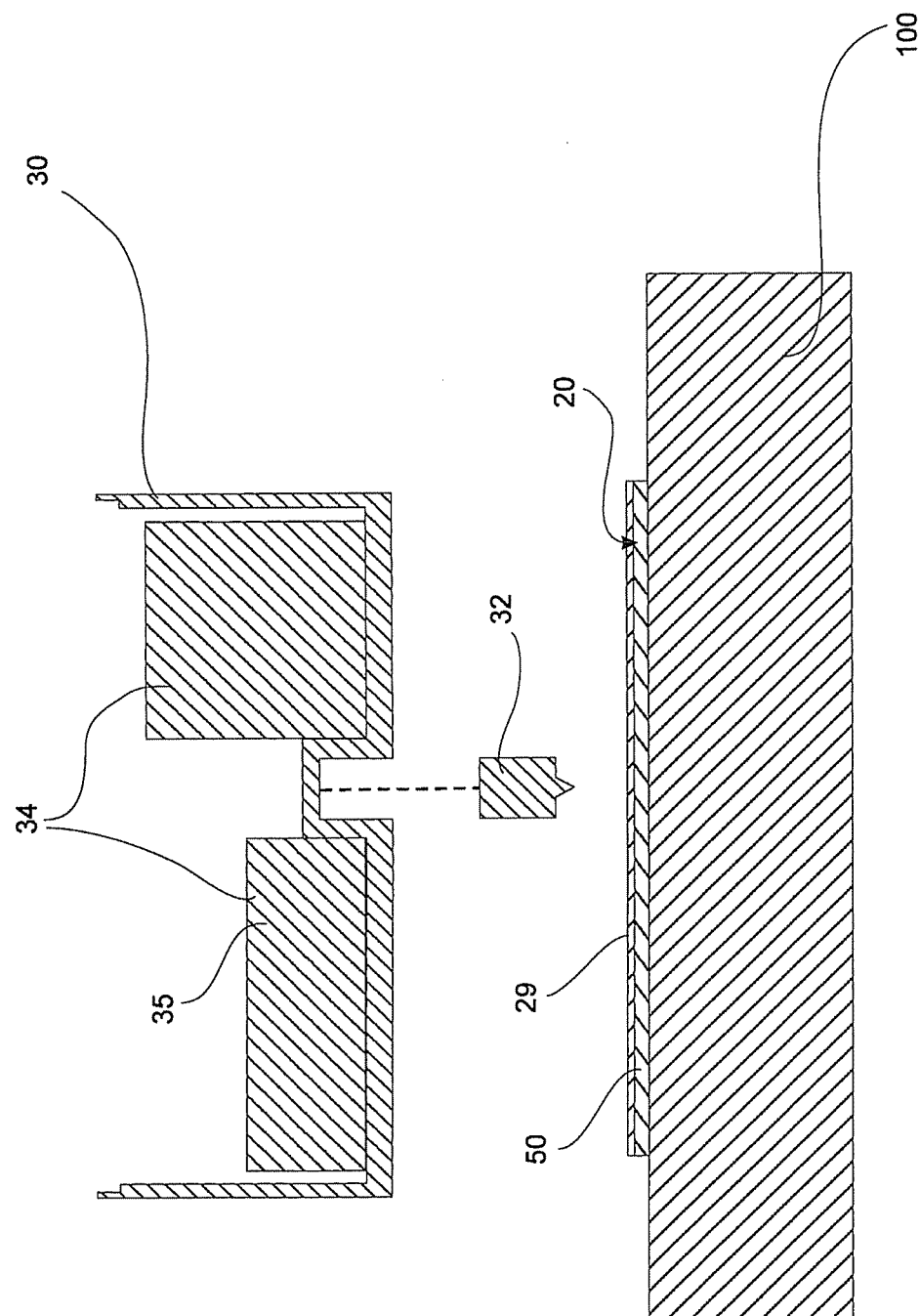
FIG. 6 shows a cross-section through a further form of embodiment of a measurement casing with a spike as the contacting means.

FIG. 6 shows in an exploded view the placing of a measurement casing 30 in position on a structural component 100, and the establishment of contact with the measurement sensor 20 with the aid of the contacting means 32. In this form of embodiment the contacting means 32 is provided in the form of a spike, which is accommodated in a depression in the measurement casing 30. Here the dashed line indicates the direction of accommodation of the spike 32 in the measurement casing 30. Here the spike can be attached in the depression of the measurement casing 30, but does not have to be, since in the releasably attached state of the measurement casing 30 on the structural component 100 it is prevented from falling out. In the measurement casing 30 itself further processing means 34 are in turn provided, wherein a board 35 of the further processing means 34 is provided with a signal amplifier and an initial evaluation device. The further processing means 34 are in signal contact with the contacting means 32, although this contact is not shown in detail in this schematic representation, and can, for example, take place by means of a signal cable, which is routed through a sealed opening in the measurement casing 30 to the further processing means 34.

In FIG. 6 a measurement sensor 20 is vapour-deposited onto a structural component 100. Under an upper passivation layer 29 this vapour-deposited measurement sensor 20 has a piezo-electric element 50. In the state that is shown in FIG. 6, that is to say, at the point in time at which the measurement casing 30 has not yet been placed in position, the passivation layer 29 is still undamaged and the piezo-electric element 50 is completely protected. In this state, by virtue of the independent mode of operation of the piezo-electric material, measurement signals are already being generated, but since contact has not yet been established, these are not yet forwarded to the further processing means 34.

Figure 7:
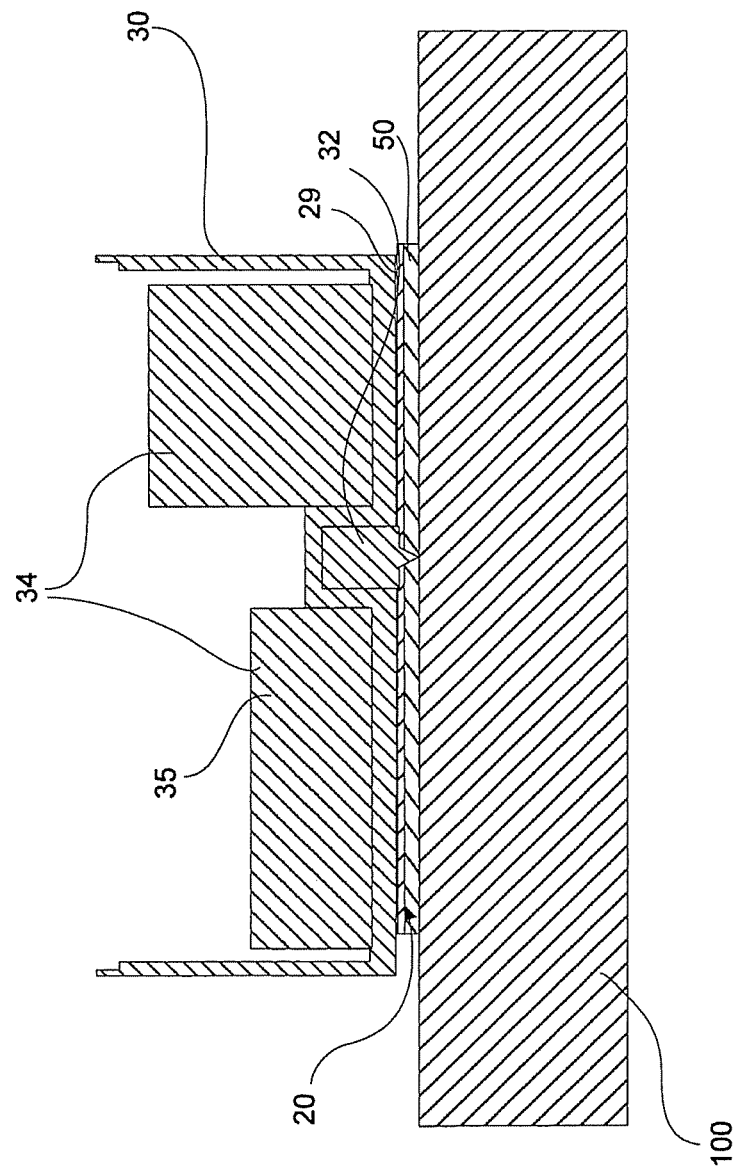
FIG. 7 shows a cross-section through the form of embodiment as per FIG. 6 in the releasably attached state.

FIG. 7 shows the form of embodiment as per FIG. 6 after the measurement casing has been placed in position. In this situation the spike, as the contacting agent 32, is already accommodated in the depression in the measurement casing 30 provided for this purpose, and has a communicative connection with the further processing means 34, in particular with the board 35. As a result of placing the measurement casing 30 in position the spike has penetrated through the passivation layer 29, and is now in contact with the piezo-electric element 50 of the measurement sensor 20. By the placing of the measurement casing 30 in position and its releasable attachment, which can be executed, for example, by means of one of the methods as has been described with respect to FIGS. 3 and 4, the establishment of contact with the piezo-electric element 20 thus takes place automatically. Here also more than one spike can be arranged in the peripheral direction around the structural component 100 for the contacting means 32. In this manner it is also possible for different regions of the measurement sensor 20 to register separate measurements, so that a force distribution within the structural component 100 can also be measured.

Figure 8:
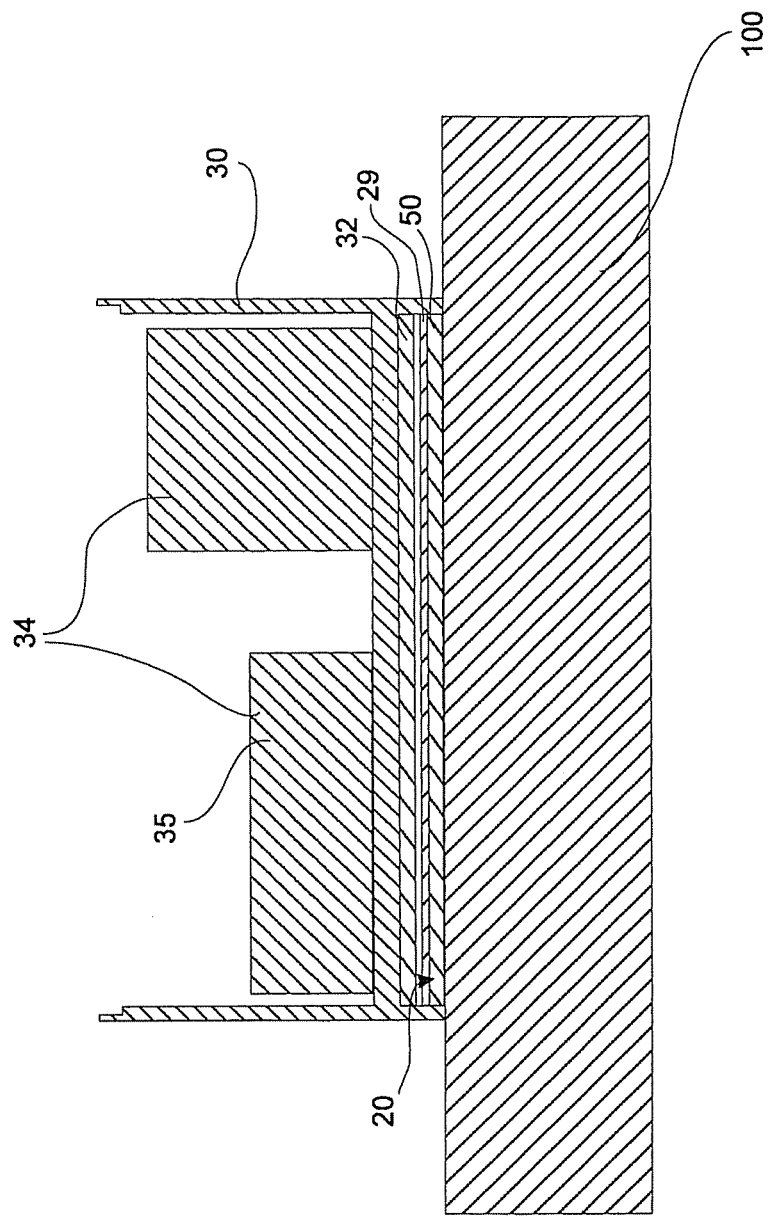
FIG. 8 shows a cross-section through a further form of embodiment with wireless contacting means in the releasably attached state.

In FIG. 8 an alternative form of embodiment in terms of the contacting means 32 can be discerned; this is in the state in which it is placed upon and releasably attached to the structural component 100. Here the transfer of the measurement signals from the measurement sensor 20 to the measurement casing 30 and its further processing means 34 takes place by means of utilisation of the capacitative effect. Here the contacting means 32 is arranged over almost the whole of the surface underneath the measurement casing 30, so that it can form a first part of a capacitor element. Amongst other duties, the measurement sensor 20 serves to form the second part of this capacitor, so that measurement signals generated by the piezo-electric element 50 of the measurement sensor 20 can be transmitted from the measurement sensor 20 by means of the capacitative effect and the contacting means 32 to the further processing means 34 in the measurement housing 30. In this case also, by means of the arrangement of the measurement housing 30 and the releasable attachment to the structural component 100, as has been elucidated in detail for example in FIGS. 3 and 4, the establishment of contact with the piezo-electric element 50 is generated automatically.

Figure 9:
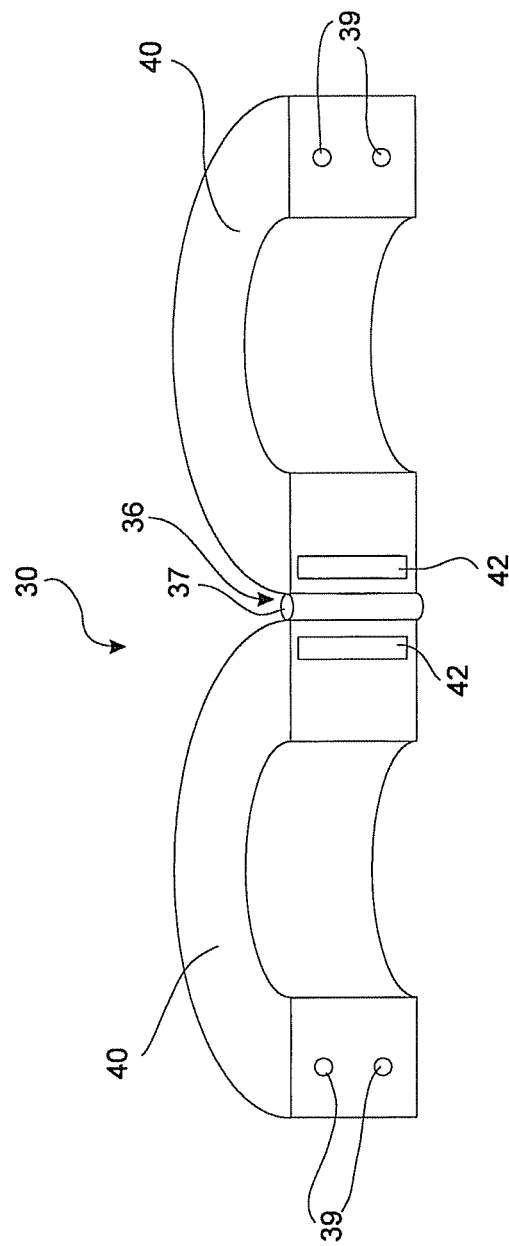
FIG. 9 shows an isometric representation of a measurement casing with a collar design and hinge.

FIG. 9 shows an isometric representation of a collar solution for the measurement casing 30. This measurement casing 30 is equipped with two segments 40, which are connected with one another by means of a hinge 37, as part of the connecting means 36. By means of this hinge 37 the two segments 40 can be closed up onto one another, so that a completely encompassing collar ensues as the measurement casing 30, which can encompass a structural component 100, not represented in this figure. By means of the encompassing the releasable attachment to the structural component 100 can be generated such that threaded means of connection 38 are placed through holes 39 and in this manner the internal diameter of the segments 40 formed as a collar can be reduced to the effect that a surface pressure ensues between the segments 40 and the structural component 100, and thus a releasable attachment. Forms of embodiment as per FIG. 9 are furthermore provided with contact surfaces 42 on each segment 40, which by means of the closing up together of the two segments 40 via the hinge 37 come into contact with one another. In this manner various further processing means 34 can be provided in the two segments 40, for example, a board 35 in the first segment 40 and a power supply in the form of a battery in the second segment 40; these communicate with one another via the contact surfaces 42 and in particular can exchange measurement signals and/or further processing signals.

Figure 10:
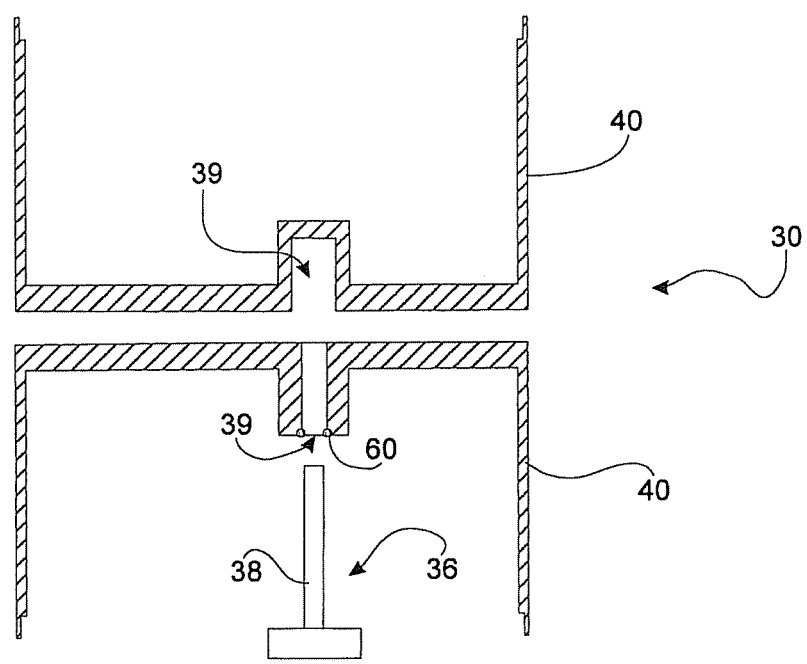
FIG. 10 shows a cross-section through an internal form of embodiment of a connecting means.

In FIGS. 10 to 13 various options are represented for the manner in which the connecting means 36 can be configured. Thus FIG. 10 shows one option for connecting the two segments 40 of a measurement casing 30 with one another, as is represented, for example, in FIGS. 3 and 4. By means of this connection of the two segments 40 the internal diameter of a measurement casing 30 shaped as a collar is reduced, so that a releasable attachment takes place by means of surface pressure with the structural component 100. In the form of embodiment as per FIG. 10 the threaded means of connection 38 is fed through corresponding holes 39 in the two segments 40, wherein in one of the holes, namely in the upper segment 40 in FIG. 10, a thread, not represented, is provided, into which the threaded means of connection 38 can engage. Since the connection here takes the form of a screw connection from the interior of the measurement casing 30, the opening into the measurement casing, which is formed by the lower hole for the threaded means of connection 39, must be sealed by means of sealing agents 60 in the form of O-rings. In this manner it is also ensured that even as a result of capillary effects no fluid can penetrate into the interior of the measurement casing 30.

Figure 11:
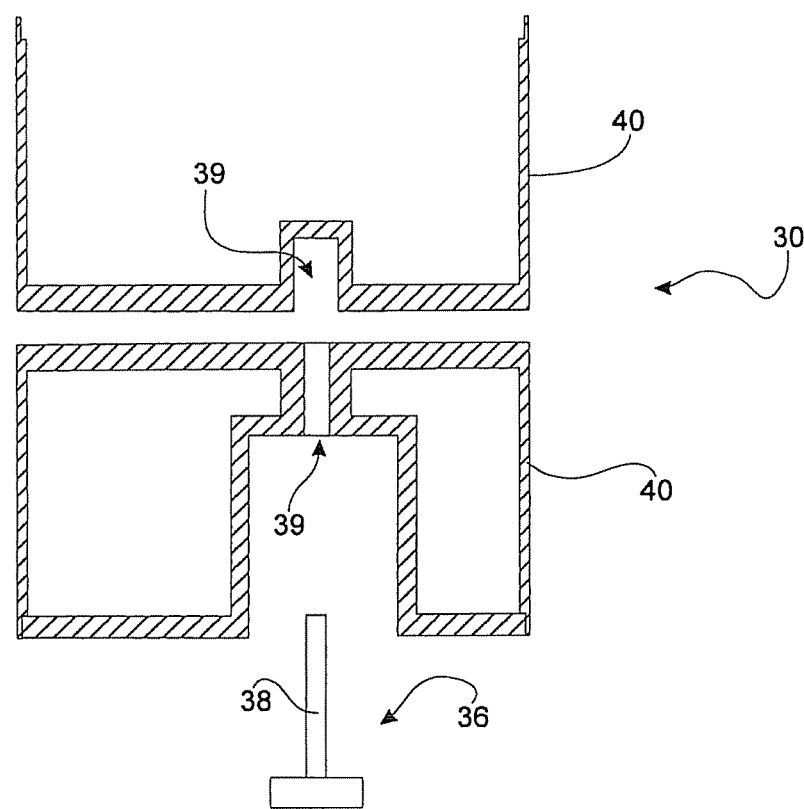
FIG. 11 shows a cross-section through an external form of embodiment of a connecting means.

So as to be able to exclude any unpredictable behaviour of the sealing agents 60, an alternative is shown in FIG. 11. There the segment 40 includes an outward protuberance, which is completely closed against the interior of the segment 40 and through which a threaded means of connection 38 can be fed to the corresponding hole 39 for the threaded means of connection 38. Here too a thread not represented is again provided in the upper hole 39 of the upper segment 40 of the measurement housing 30, into which the threaded means of connection 38 can engage. In contrast to the form of embodiment as per FIG. 10 here no form of contact exists via the two holes 29 for the threaded means of connection with the interior of the measurement casing 30, so that it is possible to dispense with a sealing agent 60 in this form of embodiment.

Figure 12:
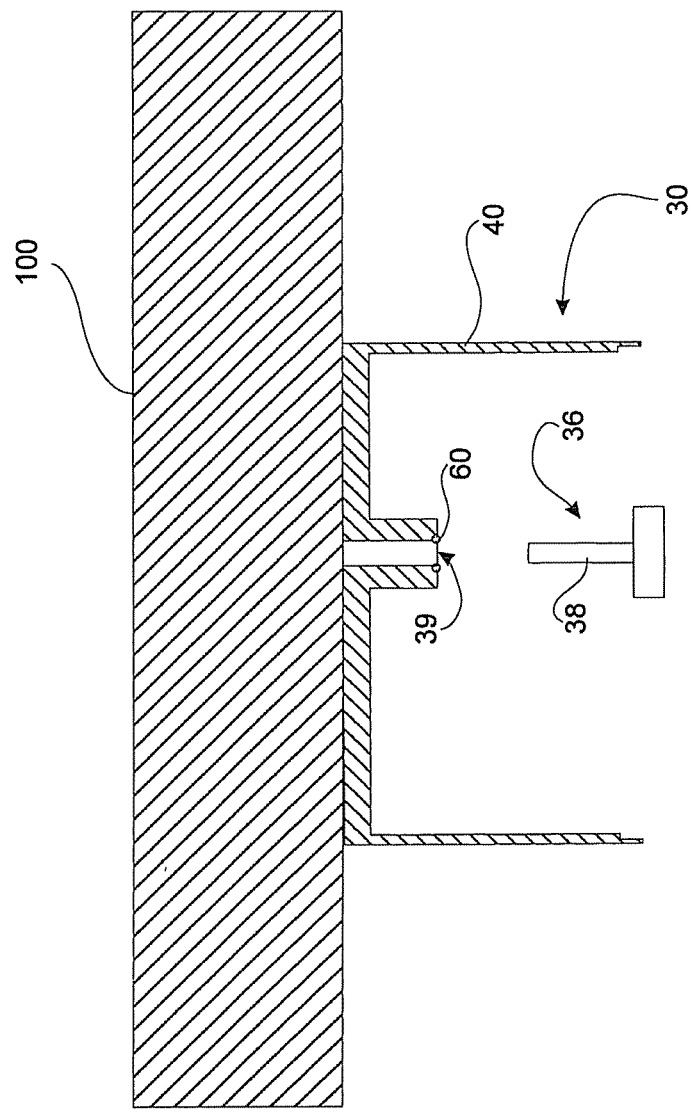
FIG. 12 shows a cross-section through a further form of embodiment with connecting means from the interior of the measurement casing.

FIG. 12 shows the attachment in the form of an alternative to the reduction of the internal diameter by the moving together of the individual segments as per FIGS. 10 and 11.

Here a grub screw is used as the threaded means of connection 38; this is inserted from the interior of a segment 40 through a hole 39 for the threaded means of connection 38. This threaded means of connection 38 thus makes contact with the structural element 100 and is jammed against the latter. So as to be able to ensure a reliable releasable attachment of the measurement casing 30 to the structural component 100, it can be advantageous to provide a multiplicity of such threaded means of connection 38, so that, in a similar manner to Christmas tree stands a radial restraint around the full periphery is effected and thus a radial releasable attachment around the full periphery of the measurement casing 30 to the structural component 100. Here it is advantageous if there is an odd number of threaded means of connection 38, so as to enable easier centring of the measurement casing 30 relative to the structural component 100. In a similar manner to FIG. 10 here too a sealing agent 60 in the form of O-rings must be provided as a result of the opening to the interior of the measurement casing 30, so as to seal the holes 39 for the threaded means of connection 38.

Figure 13:
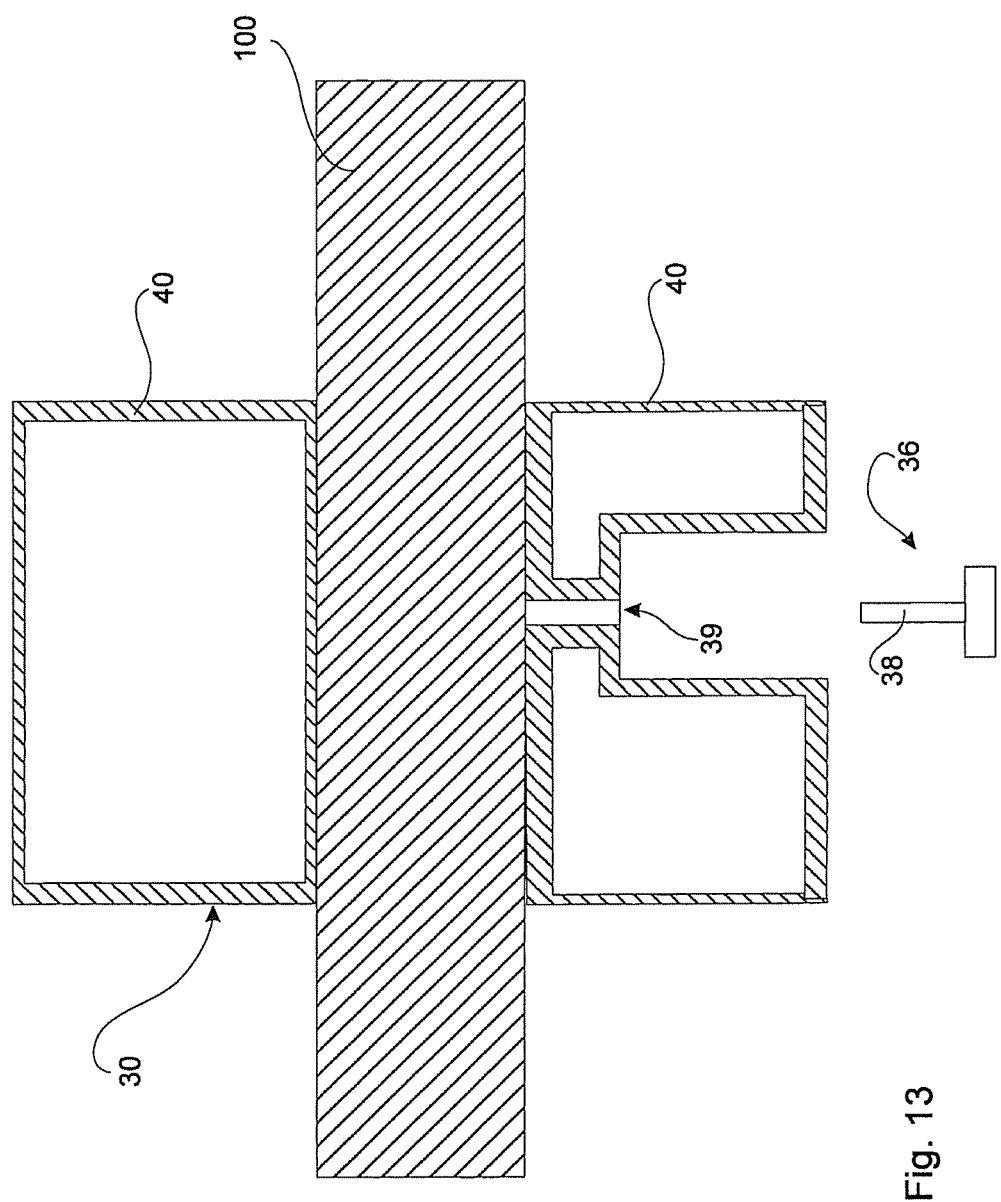
FIG. 13 shows a cross-section through a further form of embodiment with connecting means from the exterior of the measurement casing.

FIG. 13 shows a combination of the solution from FIG. 12 with the solution from FIG. 11. Here a protuberance has once again been provided in the lower segment 40 of the measurement casing 30, through which feature the threaded means of connection 38 can be fed to the related hole 39, without the need for any contact to be made with the interior of the measurement casing 30. In this manner the unpredictable behaviour of the sealing agent 60 can be completely excluded.

With regard to FIGS. 12 and 13 it is to be noted that the holes 39 with the threaded means of connection 38 are equipped with appropriate threads, which are again not represented in the two figures. It is a further option to develop the design of the connecting means 36 such that they cannot make direct contact with the structural component 100, but rather act on wall surfaces of the respective segments 40, and thus reduce the internal diameter of an opening in the measurement casing 30 by means of plastic and/or elastic deformation of these wall surfaces, as a result of which the releasable attachment to the structural component 100 is achieved. Also in such a configuration the use of sealing agents 60 can be dispensed with such that the screws are arranged completely in the interior of the measurement casing 30 and there is no form of contact with the external region outside the measurement casing 30.

Figure 14:
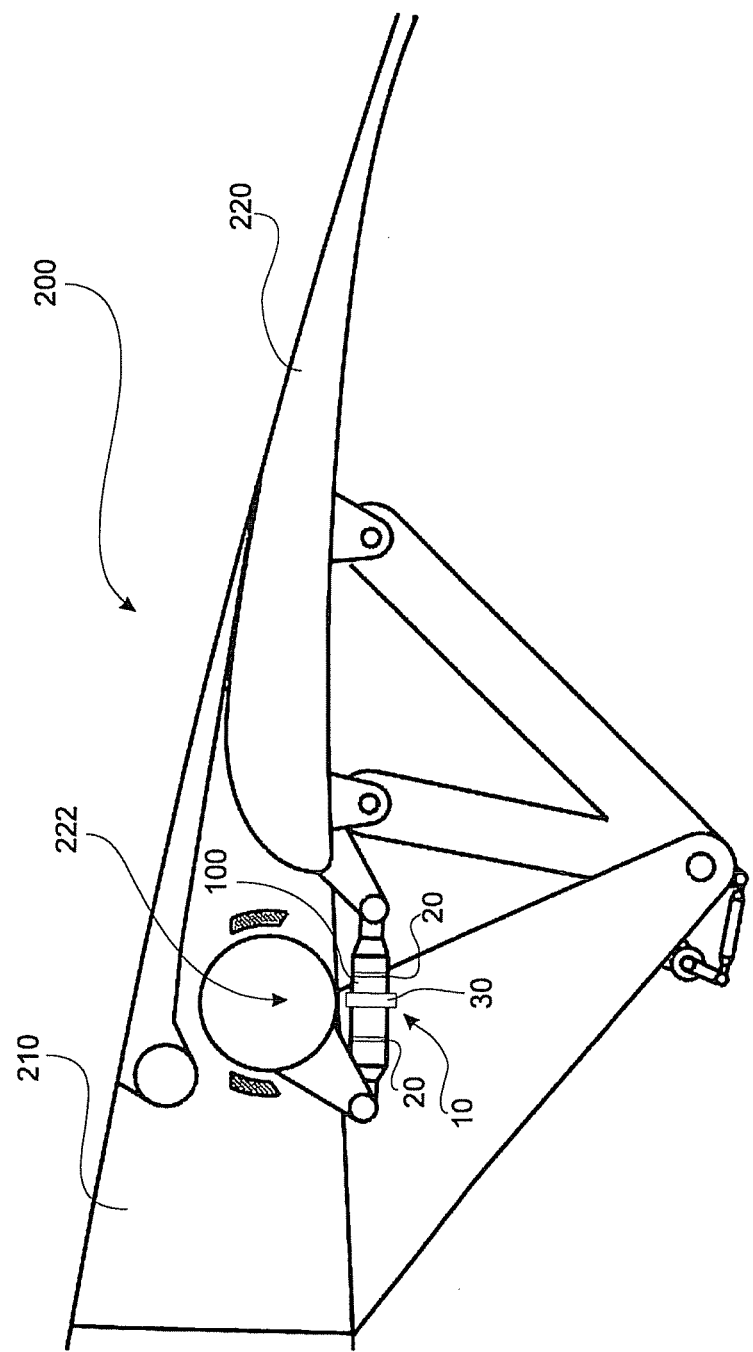
FIG. 14 shows a schematic cross-section through a high-lift device with a measurement device mounted.

FIG. 14 shows the deployment of a measurement device 10 on a high-lift device 200 of an aeroplane. Here the high-lift device 200 has a main wing surface 210, of which only a part is represented in the part-section of FIG. 14. At the right-hand end, that is to say, at the trailing edge with reference to the flight direction, a regulating flap 220 is provided on the high-lift device 200. This regulating flap 220 can be moved into various positions relative to the main wing surface 210. This movement is undertaken by an actuator 222, which is mounted on the main wing surface such that it can rotate, and has a structural component 100 in the form of a rod, which is connected with the regulating flap 220. By the rotation of the actuator 222 the structural component 100 is moved rearwards and pushes the regulating flap 220 rearwards away from the main wing surface 210. The exact movement of the regulating flap 220 is thereby prescribed by a kinematic lever mechanism, which also connects the regulating flap 220 with the main wing surface 210.

During the adjustment process force is therefore exerted by the actuator 222 and transferred via the structural component 100 in the form of a push rod. The structural component 100 is therefore loaded in compression during the extension of the regulating flap 220. This compression loading can be detected by the measurement sensors 20 provided on the structural component 100 and the signals generated are further processed by the measurement casing 30 and the therein arranged further processing means 34 as a signal. This further processing can, for example, be located in the routing to the flight control system, which controls the extension of the regulating flap 220 as a function of the measured values, in other words as a function of the actual force conditions in the structural component 100. Here it is now possible to adapt the extension process such that, for example, with high wind loads the extension takes place more slowly, or is even halted for a short time, so as to prevent any overloading of the structural component 100. In this manner the actual maximum force in the structural component 100 and therewith any related plastic deformations of sub-regions of the structural component 100 can also be registered via the measurement by means of the measurement device 10.

The description given above also applies, needless to say, to the reverse case of the retraction of the regulating flap 220, that is to say, with a tensile loading in the structural component 100.

Here in the case of the form of embodiment as per FIG. 14, a plurality of measurement sensors 20 are also applied on the structural component 100, in this case three measurement sensors 20. Thus the measurement casing 30, for example after pre-defined maintenance intervals, can be moved onto another measurement sensor 20, so as to anticipate any possible wear on the measurement device 30, and any faulty measurements resulting from this.

Furthermore alternatively or also additionally one or a plurality of measurement devices 10 can be provided on the kinematic lever mechanism for the movement of the regulating flap 220. Since relative movements and thus varying force conditions arise there also, a monitoring of the actual force conditions in the levers is possibly advantageous there also.

REFERENCE SYMBOLS

10 Measurement device
20 Measurement sensor
22 Bonding agent
24 Insulation layer
26 Measurement sensor material
28 Contact layer
29 Passivation
30 Measurement casing
31 Cover
32 Contacting means
34 Further processing means
35 Board
36 Connecting means
37 Hinge
38 Threaded means of connection
39 Holes for threaded means of connection
40 Segment of the measurement casing
42 Contact surfaces
48 Threaded means of connection
50 Piezo-electric element
60 Sealing agent
100 Structural component
200 High-lift device
210 Main wing surface
220 Regulating flap
222 Actuator for regulating flap

The invention claimed is:

1. A measurement device for the measurement of forces in structural components, comprising:

a measurement sensor, which is embodied such that it is connected in a force-fit and/or form-fit manner with the structural component and generates measurement signals as a function of force transfers in the structural component; and a measurement casing placed upon the measurement sensor, which has a contactor for establishing contact to the measurement sensor at the structural component, so as to receive the measurement signals generated by the measurement sensor, and a processor for the further processing of the received measurement signals, wherein the measurement casing has at least one connector, which is embodied for purposes of positioning and releasable attachment of the measurement casing on the structural component, wherein by the releasable attachment using the contactor, the contactor of the measurement casing establishes contact with the measurement sensor for the reception of the measurement signals.

2. The measurement device in accordance with claim 1, wherein the contactor is designed for a wireless transfer of the measurement signals from the measurement sensor to the measurement casing.

3. The measurement device in accordance with claim 1, wherein the contactor is designed for a tangible transfer of the measurement signals from the measurement sensor to the measurement casing.

4. The measurement device in accordance with claim 1, wherein the measurement sensor is designed for this purpose to be of integral design with the structural component.

5. The measurement device in accordance with claim 1, wherein the measurement sensor is designed for this purpose to be deposited onto the structural component.

6. The measurement device in accordance with claim 1, wherein the measurement sensor is embodied over a large surface area, so as to cover a larger area of the structural component than the measurement casing.

7. The measurement device in accordance with claim 1, wherein for purposes of generation of the measurement signal the measurement sensor is equipped with at least one piezoelectric element.

8. The measurement device in accordance with claim 1, wherein the processor has a wireless device for purposes of transmitting the signals received from the measurement sensor.

9. The measurement device in accordance with claim 1, wherein the processor is equipped with at least one board.

10. The measurement device in accordance with claim 1, wherein the measurement casing is sealed with sealing agents against the penetration of solid or fluid components.

11. The measurement device in accordance with claim 1, wherein the measurement casing is embodied in the form of a collar, which encompasses the structural component.

12. The measurement device in accordance with claim 1, wherein the at least one connector of the measurement casing has a hinge.

13. The measurement device in accordance with claim 1, wherein the measurement casing is composed of a plurality of segments.

14. The measurement device in accordance with claim 1, wherein the measurement casing is composed of a plurality of segments and wherein individual segments of the measurement casing are provided with contact surfaces, so as to transfer measurement signals or further processing signals between the individual segments of the measurement casing.

15. The measurement device in accordance with claim 13, wherein the at least one connector has at least one threaded connection, wherein individual segments of the measurement casing are connected with one another such that the measurement casing is attached to the structural component by surface pressure.

16. The measurement device in accordance with claim 13, wherein individual segments of the measurement casing are provided with contact surfaces, so as to transfer measurement signals or further processing signals between the individual segments of the measurement casing.

17. The measurement device in accordance with claim 13, wherein the at least one connector has at least one threaded connection, wherein individual segments of the measurement casing are connected with one another such that the measurement casing is attached to the structural component by surface pressure, and wherein individual segments of the measurement casing are provided with contact surfaces, so as to transfer measurement signals or further processing signals between the individual segments of the measurement casing.

18. The measurement device in accordance with claim 1, wherein the measurement casing has a closable cover.

19. A measurement device for the measurement of forces in a structural component, comprising:

a measurement sensor connected in a force-fit and/or form-fit manner with the structural component to generate measurement signals as a function of force transfers in the structural component; and a measurement casing disposed upon the measurement sensor, which has a contactor for establishing contact to the measurement sensor at the structural component, so as to receive the measurement signals generated by the measurement sensor, and a processor for the further processing of the received measurement signals, wherein the measurement casing has at least one connector for positioning and releasable attachment of the measurement casing on the structural component, wherein by the releasable attachment using the contactor, the contactor of the measurement casing establishes contact with the measurement sensor for the reception of the measurement signals;

wherein the measurement casing comprises a plurality of segments and wherein individual segments of the measurement casing are provided with contact surfaces, so as to transfer measurement signals or further processing signals between the individual segments of the measurement casing.

* * * * *